United States Patent
Stankus (10) Patent No.: US 10,342,474 B2
(45) Date of Patent: Jul. 9, 2019

(54) SYSTEM FOR THE ANALYSIS OF THE DAILY HEART RHYTHM AUTONOMIC NERVOUS SYSTEM BALANCE

(71) Applicant: UAB METAPRO HOLDING, Vilnius (LT)

(72) Inventor: Albinas Stankus, Palanga (LT)

(73) Assignee: UAB METAPRO HOLDING, Vilnius (LT)

( * ) Notice: Subject to any disclaimer, the term of this patent is extended or adjusted under 35 U.S.C. 154(b) by 94 days.

(21) Appl. No.: 15/521,279

(22) PCT Filed: Apr. 13, 2015

(86) PCT No.: PCT/IB2015/052676
§ 371 (c)(1),
(2) Date: Apr. 21, 2017

(87) PCT Pub. No.: WO2016/067119
PCT Pub. Date: May 6, 2016

(65) Prior Publication Data
US 2017/0311867 A1    Nov. 2, 2017

(30) Foreign Application Priority Data

Oct. 27, 2014    (LT) ..................................... 2014 125

(51) Int. Cl.
*A61B 5/0456*    (2006.01)
*A61B 5/00*    (2006.01)
(Continued)

(52) U.S. Cl.
CPC ........ *A61B 5/4035* (2013.01); *A61B 5/02405* (2013.01); *A61B 5/0452* (2013.01);
(Continued)

(58) Field of Classification Search
None
See application file for complete search history.

(56) References Cited

U.S. PATENT DOCUMENTS

| 5,176,133 A | 1/1993 | Czeisler et al. |
| 5,304,212 A | 4/1994 | Czeisler et al. |

(Continued)

FOREIGN PATENT DOCUMENTS

| EP | 2 447 866 A1 | 5/2012 |
| JP | 2004283523 A | 10/2004 |
| WO | WO 2013/184627 A1 | 12/2013 |

OTHER PUBLICATIONS

English language Abstract of JP 2004283523 A (Oct. 14, 2004).
(Continued)

*Primary Examiner* — Kennedy Schaetzle
(74) *Attorney, Agent, or Firm* — Hershkovitz & Associates, PLLC; Abe Hershkovitz (57) ABSTRACT

The present invention collects data on circadian intervals between two cardiac contractions (RR intervals) and, on the basis of the collected data on circadian RR intervals, provides a system for analysis of the human circadian heart rhythm autonomic nervous system balance, and analysis of heart rate (HR). The invention focuses on HR fluctuations that are divided into three groups: slow fluctuations of the circadian period, higher frequencies compared with circadian, and chaotic. The division into parts is executed by applying adequate empiric and mathematical methods to determine a series of envelope curves, closely and individually related to the principal circadian series, followed by their separation from the input HR series, and then applying HR variability (HRV) methods to increase accuracy of the analysis of HRV results and add new HR regulation criteria to the analysis outcomes.

12 Claims, 11 Drawing Sheets

(51) Int. Cl.
*A61B 5/024* (2006.01)
*A61B 5/0452* (2006.01)
*G16H 50/20* (2018.01)
*G16H 10/60* (2018.01)
*G16H 15/00* (2018.01)

(52) U.S. Cl.
CPC .......... *A61B 5/0456* (2013.01); *A61B 5/4857* (2013.01); *A61B 5/7203* (2013.01); *A61B 5/743* (2013.01); *G16H 10/60* (2018.01); *G16H 15/00* (2018.01); *G16H 50/20* (2018.01)

(56) References Cited

U.S. PATENT DOCUMENTS

| | | |
|---|---|---|
| 2004/0138716 A1 | 7/2004 | Kon et al. |
| 2004/0193066 A1 | 9/2004 | Carlson et al. |
| 2005/0001512 A1 | 1/2005 | Noguchi et al. |
| 2007/0219455 A1 | 9/2007 | Wong |
| 2008/0065177 A1 | 3/2008 | Casper et al. |
| 2010/0198092 A1* | 8/2010 | Jimenez-Acquarone ............ A61B 5/02405 600/515 |
| 2010/0292597 A1 | 11/2010 | Watanabe et al. |
| 2011/0144528 A1 | 6/2011 | Gurley |
| 2011/0193779 A1 | 8/2011 | Williams |
| 2012/0078318 A1 | 3/2012 | Kirchner et al. |
| 2013/0218030 A1 | 8/2013 | Barroso et al. |

OTHER PUBLICATIONS

Helong Li et al., "Hilbert-Huang Transform for Analysis of Heart Rate Variability in Cardiac Health", IEEE/ACM Transactions on Computational Biology and BIOI Nformatics. IEEE Service Center. New York. NY. US. vol. 8. No. 6, Nov. 1, 2011, pp. 1557-1567, XP058005200, ISSN: 1545-5963. DOI: 10.1109/TCBB.2011.43.

A. Stankus et al., "Frequency Bands Selection Based on 24-Hour Heart Rate Using Hilbert-Huang Transform", Cybernetics and Systems Analysis, vol. 50, No. 2, Mar. 1, 2014, pp. 297-303, XP055207988, ISSN: 1060-0396, DOI: 10.1007/s10559-014-9617-5.

Roberto Refinetti et al., "Procedures for numerical analysis of circadian rhythms", Biological Rhythm Research, vol. 38, No. 4, Aug. 1, 2007, pp. 275-325, XP055207964, ISSN: 0929-1016, DOI: 10.1080/09291010600903692.

Heart Rate Variability: Standards of Measurement, Physiological Interpretation, and Clinical Use, Circulation, 93, (1996), pp. 1043-1065.

Heart Rate Variability: Standards of Measurement, Physiological Interpretation, and Clinical Use, European Heart Journal, 17, published by the American Heart Association, Inc.; European Society of Cardiology, (1996), pp. 354-381.

Stephane Mallat, "A Wavelet Tour of Signal Processing," Third Edition: The Sparse Way. Academic press of Elsevier, 2009, 805 pp., ISBN-13: 978-0123743701.

Burden, Richard L., Faires, J. Douglas, "Numerical Analysis", 2004. Belmont: Brooks/Cole, 2011, p. 872.

Spaeth, Helmuth. Cluster-Analyse-Algorithmen zur Objektklassifizierung and Datenreduktion, Verfahren der Datenverarbeitung, Muenchen: R.Oldenbourg, 1975, p. 71.

Huang N.E., Shen, Z., Long, S. et al., "The Empirical Mode Decomposition and the Hilbert Spectrum for Nonlinear and Non-Stationary Time Series Analysis". Proc. Royal Soc. London Series A, 1998, vol. 454, pp. 903-995.

Ming-Chya Wu and Chin-Kun Hu, Application of Empirical Mode Decomposition to Cardiorespiratory Synchronization. S.K. Dana et al. (eds.), Complex Dynamics in Physiological Systems: From Heart to Brain, Understanding Complex Systems, Springer Science+ Business Media B.V. 2009.

Nelson W, Tong YL, Lee JK, Halberg F, "Methods for cosinor-rhythmometry". Chronobiologia. 1979, 6(4), pp. 305-323.

Cornelissen G., "Cosinor-based rhythmometry". Theor Biol Med Model. 2014, 11; 11(1):16.

Bingham C., Arbogast B., Cornelissen Guillaume G., Lee JK, Halberg F., "Inferential statistical methods for estimating and comparing cosinor parameters". Chronobiologia, 1982, vol. 9, pp. 397-439.

International Search Report of PCT/IB2015/052676 dated Aug. 26, 2015.

* cited by examiner

Fig. 1. System for the analysis of the circadian heart rhythm autonomic nervous system balance Fig. 2. Flow chart of the analysis system block for heart rhythm artifacts and arrhythmias removal, chaotic part detection and series interpolation Fig. 3. Flow chart of the block for the heart rhythm bimodal distribution and analysis of the detected modes Fig. 4. Flow chart of the block for the identification of the circadian period of the heart rhythm Fig. 5. Block for the analysis of the SNS and PNS regulation criteria of the heart rhythm variable part Fig. 6. Content of the data presented by the reporting block.

Fig. 7. RR interval series reporting graph

Fig. 8. Histogram of the block according to Fig. 2 chaotic series

HR daily period characteristics

| | SNS | PNS | General |
|---|---|---|---|
| RR mean, ms | 894 | 1183 | 1028 |
| RR standart deviation, ms | 83 | 88 | 167 |
| RR number | 47095 | 40756 | 87792 |
| Indices (RR number ratio) | 0,54 | 0,46 | 1 |
| Duration, (hh:mm:ss) | 13: 4:55 | 11:19:16 | 24:23: 3 |
| Coefficient of divergention, ms | | 289 | |
| Middle level of RR value, ms | | 1048 | |
| Coefficient of distribution asymmetry | | 1,16 | |
| Duration of the day, (hh:mm:ss) | 6:39:56 | 0:45: 5 | |
| Duration of the night, (hh:mm:ss) | 0:30:40 | 7:29:20 | |
| Duration of free time, (hh:mm:ss) | 5:54:19 | 3: 4:51 | |
| Daily HR time asymmetry between the SNS and PNS | | 8,87 | |
| HR night time asymmetry between the SNS and PNS | | 14,65 | |
| Time ratio between the SNS and PNS another time | | 1,92 | |
| Variance of chaos, ms2 | | | 54 |

Fig. 9. Table containing data obtained according to Fig. 2 and Fig. 3 blocks

Fig. 10. Image of the histogram of the sequence according to Fig. 3

Fig. 11. Histogram of the RR interval bimodal distribution according to Fig. 3 block The results of every (2) hour

| | xRR(PNS), ms | sdRR(PNS), ms | xRR(SNS), ms | sdRR(SNS), ms | tud.coef | SNS/PNS (time) | SNS, s. | PNS, s. | xRR, ms | sdRR, ms | VLF (sd), ms | LF(sd), ms | HF(sd), ms | LF/HF, ms2/ms2 |
|---|---|---|---|---|---|---|---|---|---|---|---|---|---|---|
| 10:35 | 1144,17 | 73,85 | 926,64 | 79,07 | 164,84 | 1,82 | 4650,00 | 2550,00 | 1003,68 | 129,59 | 117,21 | 22,31 | 14,89 | 2,25 |
| 12:35 | 1060,12 | 25,79 | 884,89 | 56,74 | 84,18 | 87,89 | 7119,00 | 81,00 | 886,86 | 59,43 | 52,51 | 19,53 | 12,53 | 2,43 |
| 14:35 | 1060,35 | 13,57 | 811,96 | 68,75 | 132,67 | 247,28 | 7171,00 | 29,00 | 812,96 | 70,40 | 58,74 | 14,67 | 9,21 | 2,54 |
| 16:35 | 1064,83 | 29,08 | 870,62 | 72,62 | 95,57 | 63,00 | 7087,50 | 112,50 | 873,66 | 76,05 | 65,48 | 20,02 | 10,90 | 3,37 |
| 18:35 | 1078,37 | 31,80 | 922,93 | 69,58 | 176,68 | 4,05 | 5774,50 | 1425,50 | 953,71 | 88,99 | 78,99 | 24,31 | 15,29 | 2,53 |
| 20:35 | 1120,54 | 47,61 | 945,97 | 80,57 | 114,29 | 0,27 | 1521,50 | 5678,50 | 1083,65 | 90,76 | 80,65 | 18,14 | 13,52 | 1,80 |
| 22:35 | 1157,49 | 37,06 | 880,70 | 124,14 | 56,55 | 0,05 | 323,00 | 6877,00 | 1145,07 | 72,70 | 67,25 | 15,94 | 14,19 | 1,26 |
| 00:35 | 1214,08 | 60,30 | 919,84 | 76,30 | 86,69 | 0,04 | 258,50 | 6941,50 | 1203,52 | 81,92 | 75,40 | 22,89 | 17,83 | 1,65 |
| 02:35 | 1254,53 | 71,61 | 904,87 | 82,20 | 118,56 | 0,06 | 406,00 | 6794,00 | 1234,81 | 108,28 | 97,42 | 24,48 | 18,98 | 1,66 |
| 04:35 | 1236,17 | 106,28 | 898,84 | 107,24 | 96,50 | 0,08 | 505,50 | 6694,50 | 1212,48 | 136,89 | 124,82 | 28,48 | 23,23 | 1,50 |
| 06:35 | 1165,90 | 72,37 | 894,93 | 75,67 | 169,27 | 4,72 | 5941,50 | 1258,50 | 942,30 | 127,40 | 97,96 | 23,92 | 17,36 | 1,90 |
| 08:35 | 1077,57 | 37,54 | 956,04 | 51,93 | 143,73 | 3,90 | 5730,50 | 1469,50 | 980,84 | 69,52 | 55,65 | 21,55 | 16,66 | 1,67 |
| 10:35 | 1105,46 | 53,95 | 988,86 | 37,86 | 68,40 | 0,72 | 606,50 | 844,00 | 1056,71 | 74,84 | 64,90 | 20,15 | 20,12 | 1,00 |

Fig. 12. Statistical estimation of the RR interval bimodal time distribution every 2 hours Fig. 13. Time course of the circadian tonic sympatho-vagal balance according to Fig. 3

Fig. 14. Statistical evaluation of the structure of circadian period of the circadian heart rhythm Fig. 15. Diagram of the circadian period sequence of the circadian heart rhythm Fig. 16. Classical infinite impulse response three-filter system The results of every (2) hour

| | xRR(PNS), ms | sdRR(PNS), ms | xRR(SNS), ms | sdRR(SNS), ms | tud.coef | SNS/PNS (time) | SNS, s. | PNS, s. | xRR, ms | sdRR, ms | VLF (sd), ms | LF(sd), ms | HF(sd), ms | LF/HF, ms2/ms2 |
|---|---|---|---|---|---|---|---|---|---|---|---|---|---|---|
| 10:35 | 1144,17 | 73,85 | 926,64 | 79,07 | 164,84 | 1,82 | 4650,00 | 2550,00 | 1003,68 | 129,59 | 117,21 | 22,31 | 14,89 | 2,25 |
| 12:35 | 1060,12 | 25,79 | 884,89 | 56,74 | 84,18 | 87,89 | 7119,00 | 81,00 | 886,86 | 59,43 | 52,51 | 19,53 | 12,53 | 2,43 |
| 14:35 | 1060,35 | 13,57 | 811,96 | 68,75 | 132,67 | 247,28 | 7171,00 | 29,00 | 812,96 | 70,40 | 58,74 | 14,67 | 9,21 | 2,54 |
| 16:35 | 1064,83 | 29,08 | 870,62 | 72,62 | 95,57 | 63,00 | 7087,50 | 112,50 | 873,66 | 76,05 | 65,48 | 20,02 | 10,90 | 3,37 |
| 18:35 | 1078,37 | 31,80 | 922,93 | 69,58 | 176,68 | 4,05 | 5774,50 | 1425,50 | 953,71 | 88,99 | 78,99 | 24,31 | 15,29 | 2,53 |
| 20:35 | 1120,54 | 47,61 | 945,97 | 80,57 | 114,29 | 0,27 | 1521,50 | 5678,50 | 1083,65 | 90,76 | 80,65 | 18,14 | 13,52 | 1,80 |
| 22:35 | 1157,49 | 37,06 | 880,70 | 124,14 | 56,55 | 0,05 | 323,00 | 6877,00 | 1145,07 | 72,70 | 67,25 | 15,94 | 14,19 | 1,26 |
| 00:35 | 1214,08 | 60,30 | 919,84 | 76,30 | 86,69 | 0,04 | 258,50 | 6941,50 | 1203,52 | 81,92 | 75,40 | 22,89 | 17,83 | 1,65 |
| 02:35 | 1254,53 | 71,61 | 904,87 | 82,20 | 118,56 | 0,06 | 406,00 | 6794,00 | 1234,81 | 108,28 | 97,42 | 24,48 | 18,98 | 1,66 |
| 04:35 | 1236,17 | 106,28 | 898,84 | 107,24 | 96,50 | 0,08 | 505,50 | 6694,50 | 1212,48 | 136,89 | 124,82 | 28,48 | 23,23 | 1,50 |
| 06:35 | 1165,90 | 72,37 | 894,93 | 75,67 | 169,27 | 4,72 | 5941,50 | 1258,50 | 942,30 | 127,40 | 97,96 | 23,92 | 17,36 | 1,90 |
| 08:35 | 1077,57 | 37,54 | 956,04 | 51,93 | 143,73 | 3,90 | 5730,50 | 1469,50 | 980,84 | 69,52 | 55,65 | 21,55 | 16,66 | 1,67 |
| 10:35 | 1105,46 | 53,95 | 988,86 | 37,86 | 68,40 | 0,72 | 606,50 | 844,00 | 1056,71 | 74,84 | 64,90 | 20,15 | 20,12 | 1,00 |

Fig. 17. Circadian time course of the indicators of heart rhythm variability

SYSTEM FOR THE ANALYSIS OF THE DAILY HEART RHYTHM AUTONOMIC NERVOUS SYSTEM BALANCE

FIELD OF THE INVENTION

The invention relates to a system for the analysis of the human circadian heart rhythm autonomic nervous system balance including identification of diurnal periods wherein the system comprises: 1) a tool adapted for identification of the chaotic part of the R wave to R wave interval (RR) interval series and analysis of the chaotic part; 2) a tool adapted for separation of the chaotic part from RR interval series and acquisition of the clean circadian RR series; 3) a tool adapted for acquisition of the normalized RR interval series using: interpolation; resampling; and normalization; 4) a tool adapted for analysis of the heart rate bimodal distribution and modes of the normalized RR interval series; 5) a tool adapted for identification of the heart rate circadian period in the normalized RR data series; 6) a tool adapted for analysis of the heart rhythm variable part SNS and PNS regulation indicators in the normalized RR data series; and 7) a tool adapted for generation of the report on obtained results in graph and tabular form.

BACKGROUND OF THE INVENTION

Identification of the autonomic nervous system (ANS) balance within the regulation of the heart rhythm (HR) is based on the fact that the duration of every single heartbeat is determined by the effect of the sympathetic nervous system (SNS) and parasympathetic nervous system (PNS) on the heart sinus node. Due to this effect short-term phase HR acceleration and deceleration occur. However, it has been established that circadian rhythms influence fluctuations in the change of cardiovascular system day and night functions and metabolic functions. It had recently been proven that central and peripheral circadian pacemakers exercise partial direct control of the cardiovascular system and metabolic processes. This suggests that HR observation may help to safely exclude various parameters from the circadian oscillations. These parameters are of high importance for the improvement of an individual's sleep, physical and mental status and health. Their identification will help to adapt an individual to night shifts, avoid sleep disorders, optimize professional activities, increase performance, and improve sporting achievements and quality of life.

Steady slow HR is related to the tonic PNS predominance on HR regulation and fast HR is related to the tonic SNS predominance. HR is involved in the energy and blood supply to the whole body and it is readily affected by respiration, physical and nerve stimulants. Short-term HR fluctuations can be easily observed due to these stimulants. Well-known structures, such as an ANS sinus node and receptor system, participate in their development.

Beside the aforementioned regularities, HR also contains stochastic elements, such as: nerve impulsing; mediator release in the synapse or; action potential formation in the node. Processes of synthesis of various active substances, e.g., ion channel activation and inactivation and matter diffusion, could be observed at this level. This is the diffusion part of the HR process.

Heart rhythm is directly related to body energy requirements. Heart physiology shows that two main states are observed: activity and rest that are distinctly manifesting as changes of day and night rhythm. Body energy requirements are maximum at one instance and minimum at another. This is caused by the level of energy consumption which is equivalently reflected by HR. HR is the indicator of the energy consumption in the body and allows describing and easily defining the consumption ratio between two states over a period of observation. Basic bimodal distribution of HR with some deviations is usually observed; these deviations are caused by unsteadiness of external and internal body activities.

HR regulation by SNS and PNS is fairly complex. However, in the majority of cases, it is exercised through ANS, except for humoral responses. SNS effect on HR is quite slow and is related to the increase of body's energy demands due to the increase of heart rate, blood pressure and/or cardiac output. The PNS component responds much faster compared with the sympathetic component and reduces heart rate, blood pressure and/or cardiac output. At rest and during sleep proper balance between SNS and PNS is achieved very quickly. This sympatho-vagal balance is extremely important both for healthy and ill body reactions to various stimuli.

Using HR variability (HRV) methods ANS balance of short HR segments is defined as the ratio of two components of the spectrum of intervals between successive heartbeats (RR intervals): low frequencies (LF) and high frequencies (HF) ratio. One of the conditions of the analysis is stationary and linear origin of the RR series. Such conditions are possible when a subject itself is in a steady state. Otherwise, results are unsteady and hardly reproducible especially during long-term heart rate registration. The high frequency component of the heart rhythm frequently remains constant enough, whereas investigations of the low frequency component currently gives rise to doubts and criticism. Short-term (up to 5 minutes) circadian RR interval series are usually used to draw such conclusion. These calculations may be more precise when series duration is increased, and when an observation period covers a 24-hour period, the impact of the additional frequency component and unsteadiness occurs. Currently, circadian rhythm is being analyzed using HRV methods. It is clear that within 24 hours, heart rate changes not only due to the short-term external and internal stimuli but also due to the circadian biorhythm characterized by much higher dispersion. Obtained circadian RR series are composed of the sum of circadian biorhythm, various unsteady fluctuations and chaotic part.

A patient's metabolism circadian rhythm may be established by the registration of whole body temperature in various body sites (US 20110144528 (A1), U.S. Pat. No. 5,304,212 (A)) and by the measurement of the illumination of the environment (U.S. Pat. No. 5,176,133 (A), US2008065177 (A1), US 2005001512 (A1), WO 2013184627 (A1)). An analysis system is known when circadian rhythm is calculated from patient's blood carbon dioxide ($CO_2$) parameters using an implantable medical device (US 2004138716 (A1)). Recent studies show that body cells have their own circadian clocks. Gene measurements have updated these studies (US 2011193779 (A1)).

A more precise system for the estimation of circadian rhythm combining together fitting and regression analysis for a series of RR intervals (intervals between two cardiac contractions) and electrocardiographic interval (QT) series derived from the ECG (electrocardiogram) series obtained by Holter monitoring is presented in the application for the patent US 20100292597 (A1). This method is based on the cosine function application for the whole series that is used for the identification of circadian rhythm within data obtained by registering body temperature. These methods use an assumption that circadian period presents clear cosine-wave shape. However, an ordinary person works, eats, sleeps, moves, has various diseases, and changes if his heart rhythm depends on the changes of metabolism, and therefore shape of circadian period is not always present as regular cosinusoid. This causes more dynamic changes and intrinsic circadian periods of the HR. Therefore, a more precise diagnostic technique is needed able to derive a true shape of circadian HR period and its parameters from the RR interval series.

Identification of the circadian rhythm using simulation principles when the factor causing rhythm changes is known (EP2447866 (A1)) is also used. In this model, an input signal could be RR series or other signal related to the circadian dynamics of the heart rhythm, such as acti-graph presented in this patent. Autoregressive-moving-average model (AR-MAX) is applied to the combination of first signal and second input signal. Output signal, namely, circadian period, is fully dependent on periodicity of the input signal and may strongly influence the result, circadian rhythm signal. In order to represent (sharpen) circadian rhythm, a cosinor regression model is additionally used to obtain aforementioned cosine-wave shape. The method described requires registration of the additional signal, and results are linearly dependent on its representation of circadian rhythm.

Obtained series of circadian RR intervals are composed of individual circadian biorhythm and the sum of various unsteady changes. Prior inventions are not ultimately related to the principles of the regulation of heart rhythm, specifically with the peculiarities of autonomic nervous system and other systems. It has long been known that slow HR is related to the predominant effect of tonic PNS on the HR regulation and quick HR is related to the predominance of tonic SNS. Therefore, study findings do not contain results of the analysis in terms of further changes of circadian rhythm.

Published Patent Application US 20040193066 (A1) presents a heart rhythm managing system demonstrating the patient's state; it is based on the balance between SNS and PNS components and uses RR interval signal filtration in two bandwidths not limiting strictly filter characteristics, and therefore further processing results (dispersion is calculated) may differ from the data described in other known sources.

Japanese application JP2004283523 (A) describes the system for the analysis of the balance of autonomic nervous system comprising a unit for collecting circadian RR intervals, tools for artifacts and arrhythmias removal from the RR interval series, circadian period identifier and RR data series analyzer determining balance of the sympathetic nervous system (SNS) and parasympathetic nervous system (PNS).

This system for the analysis of the autonomic nervous system balance for the first time allowed determining circadian period from heart rhythm. Detection of the circadian balance of the SNS and PNS elements of the autonomic nervous system is based on well-known methods of heart rhythm variability that are used for a long time (Heart Rate Variability: Standards of Measurement, Physiological Interpretation, and Clinical Use, Circulation, 93, (1996), pp. 1043-1065; Heart Rate Variability: Standards of Measurement, Physiological Interpretation, and Clinical Use, European Heart Journal, 17, published by the American Heart Association, Inc.; European Society of Cardiology, (1996), pp. 354-381). The simplest method is employed by splitting circadian series of the heart rhythm by frequency distribution using fast Fourier transform (FFT) method. Data are collected using Holter monitors, and RR intervals are selected and arrhythmias and artifacts are excluded. Forward and backward Fourier transform is applied to circadian heart rhythm data and a variation curve is obtained. Accuracy of the analysis depends on series length and duration of the period selected from the bandwidth in the analyzed series. Basically, accuracy of the Fourier transform depends on the length of the series and number of periods of interest in this analyzed series. Consequently, only one period is present in the 24-hours series, and therefore the period discovered contains large errors and is inaccurate.

The described analysis system focus on the detection of two intersections points on the transition curve obtained after inverse Fourier transform showing on the curve, according to the inventors, changes of the vegetative nervous system 24-hours rhythm. Moreover, it is unclear what should be done with 48-hours data containing 4 points. It has not been considered that true ANS circadian rhythm due to internal hormonal fluctuations and temperature dynamics is governed by circadian metabolic rhythm possessing sinusoid shape and two intersection points. Heart rhythm follows development of the body metabolic processes; however, it is influenced also by other internal (hormones, blood pressure) and external (physical and nerve) factors. Therefore, the period of circadian heart rhythm reflects not only the main circadian metabolic rhythm of the body but also full ANS impact on the heart rhythm and exclusively may have several shorter periods and intersection points. Only circadian heart rhythm period comprising components of ANS and other components (known and unknown) could be evaluated. Obtained circadian period of heart rhythm approximated using a cosinor method to the cosine-wave shape could contain sizable errors as suggested in the aforementioned source US 201003292597 (A1).

SUMMARY OF THE INVENTION

It is therefore an object of the present invention by employing all known tools for the collecting data on circadian RR intervals to develop on the basis of the collected data on circadian RR intervals a system for the analysis of the circadian heart rhythm autonomic nervous system balance that is free of disadvantages determined in the application for the patent JP2004283523 (A). Furthermore, the present invention aims to expand methods of the analysis if HR and to apply them more widely in the medicine, ergonomics, sports and other fields requiring long-term monitoring of health status.

This object is achieved by the system for the analysis of the human circadian heart rhythm autonomic nervous system balance which increases accuracy of the analysis of HRV results and adds new HR regulation criteria to the analysis outcomes, wherein the system comprises a RR interval collection block (20), tools (110) for artifact and arrhythmias removal from RR interval series (65), an identifier for circadian period (360) and RR interval series (180), and a data analyzer finding sympathetic and parasympathetic nervous system balance, wherein the tools comprise: tools which are configured to perform the following steps after artifact and arrhythmias removal from (110) RR interval series (65): 1) identification of a chaotic part of the RR interval series (120) and analysis of the chaotic part (190); 2) separation of the chaotic part from RR interval (140) series and acquisition of a clean circadian RR series (150); 3) acquisition of a normalized RR interval series (180) using interpolation, resampling and normalization (160); 4) analysis block (200) of the heart rate bimodal distribution and modes of the normalized RR interval series (180); 5) identification of a heart rate circadian period (300) in the normalized RR data series (180); 6) analysis block (400) of the heart rhythm variable part SNS and PNS regulation indicators in the normalized RR data series (180); 7) generation of report (70) on obtained results in graph (92) and tabular (94) form.

The present invention focuses on HR fluctuations that could be divided into 3 groups: slow fluctuations of the circadian period, higher frequencies compared with circadian, and chaotic. Their division into parts is executed applying adequate empiric and mathematical methods allowing the determination of series envelope curves, closely and individually related to the principal circadian series, followed by their separation from the input HR series and, only after this procedure, HR variability methods could be applied. This method increases accuracy of the analysis of HRV results and adds new HR regulation criteria to the analysis outcomes.

Embodiments of this analysis system are presented in the invention disclosure.

According to the invention, the proposed system for the analysis of the circadian heart rhythm autonomic nervous system balance comprises tools that after removing of the artifacts and arrhythmias from the RR intervals accomplish the following steps:

Identification of the chaotic part and analysis of the chaotic series of the RR series;

separation of the chaotic part from RR interval series and acquisition of the clean circadian RR series;

acquisition of the normalized RR interval series using interpolation, resample and normalization;

analysis of the heart rhythm bimodal distribution and modes of the normalized RR interval series;

identification of the heart rhythm circadian period in the normalized RR data series;

analysis of the indicators of the heart rhythm variable part regulation by sympathetic nervous system (SNS) and parasympathetic nervous system (PNS) in the normalized RR data series;

findings report generation in graph and tabular form.

When tools for the exclusion of artifacts and arrhythmias from the RR interval series separating chaotic series from the RR series employ wave transformation method, a clean RR interval series is obtained. Normalized data series is obtained when interpolation of the circadian RR interval series is performed using cubic Hermite interpolation method.

The following steps are part of the heart rhythm bimodal distribution and modes obtained from the normalized RR data series by the analysis module:

calculation of the input histogram sequence out of normalized RR data series and histogram graphic presentation;

clustering of the normalized RR data series using k-means clustering method into two RR clusters (modes) of which the first RR cluster (first mode) involves low heart rhythm frequencies and second RR cluster (second mode) involves high heart rhythm frequencies;

calculation of the statistical characteristics of the first mode and second mode;

calculation of the probability density functions of the both modes and their histograms;

summation of the probability density histograms and their graphic presentation;

determination of the reliability of the compliance of the distribution of the summary histogram and input histogram using chi-square criteria and calculation of the summary histograms of both modes;

determination of the divergence coefficient of the summary histogram;

determination of the skewness coefficient of the heart rate and skewness coefficient of the total time in the input histogram;

tabular presentation of the statistical calculations of the RR intervals;

calculation and graphic presentation of the circadian time distribution of the RR interval within both modes;

graphic presentation of the normalized time course of the circadian tonic sympatho-vagal balance;

tabular presentation of the values of results of summary calculations of the values of RR interval analysis;

The following steps are performed by heart rhythm circadian period identification in the normalized RR data series module:

isolation of this period using continual empirical mode decomposition (Huang transform) and their gradual elimination from every residual RR interval series;

creation of the heart rhythm circadian period series and analysis of the circadian period structure.

Analysis of the circadian period structure is performed by separating circadian series of metabolic origin and heart rhythm circadian period series which is obtained using the cosinor calculation method and involves statistical evaluation of the series and parameters obtained; these results are presented in tabular and graphic form. This allows performing statistical analysis of interim HR fluctuation periods observed at specific points.

The following steps are executed by the analyzer of the SNS and PNS regulation criteria of the heart rhythm variable part:

separation of the variable part which is achieved by the subtraction heart rhythm circadian period series from the normalized RR data sequence;

filtering of the variable heart rhythm series using infinite impulse response three-filter restriction method allowing separation of RR interval time series of different frequencies: very low frequency (VLF), low frequency (LF) and high frequency (HF) RR intervals time series;

calculation of the dispersion and mean standard deviations and of the RR intervals time series;

evaluation of the heart rhythm variability;

tabular and graphic presentation of the results of evaluation of heart rhythm variability.

Evaluation of the heart rhythm variability is carried out:

for the very low frequency filter (VLF, from 0 Hz to 0.04 Hz) determining passband edge frequency equal to 0.035 Hz and stopband edge frequency equal to 0.04 Hz;

for low frequency band filter (LSm 0.04-0.15 Hz) determining stopband edge frequency at low frequency side equal to 0.035 Hz, and at high frequency side equal to 0.0155 Hz, passband edge frequency at low frequency side equal to 0.04 Hz, and at high frequency side equal to 0.15 Hz;

for high frequency band filter (HF, 0.15-0.40 Hz) determining stopband edge frequency at low frequency side equal to 0.145 Hz, and at high frequency side equal to 0.45 Hz, passband edge frequency at low frequency side equal to 0.15 Hz, and at high frequency side equal to 0.40 Hz.

During the evaluation of the heart rhythm variability dispersion ratio for every time frame within low frequency (LF) and high frequency (HF) bands presenting phase balance of SNS and PNS, changes are calculated.

BRIEF DESCRIPTION OF THE FIGURES

Preferred embodiments for the implementation of the present invention are detailed below together with references to the attached diagrams involving:

FIG. 17: Circadian time course of the indicators of heart rhythm variability.

DETAILED DESCRIPTION OF THE INVENTION (DESCRIPTION OF THE PREFERRED EMBODIMENT)

Figure 1:
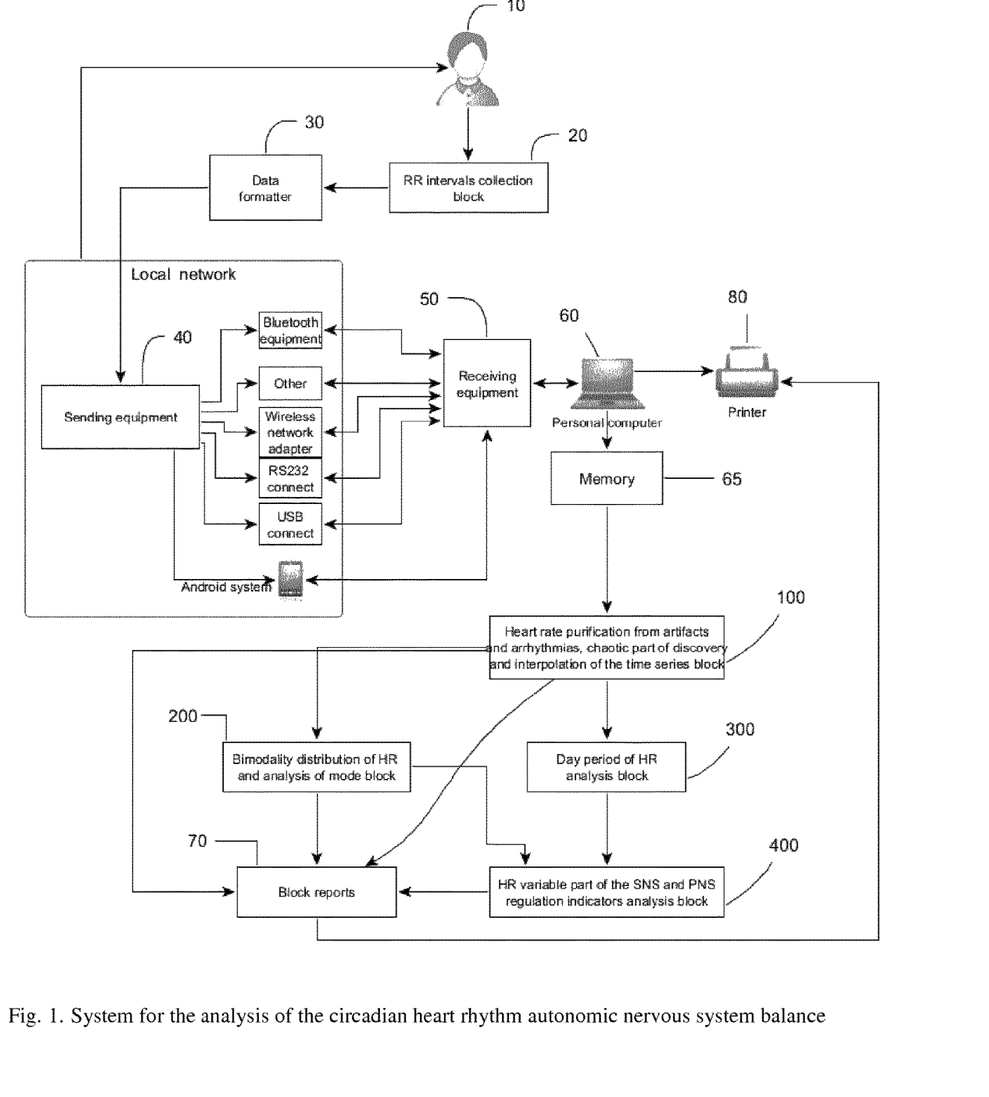
FIG. 1: System for the analysis of the circadian heart rhythm autonomic nervous system balance.

A subject's (10) physiological signals enter heart rhythm RR interval collection block 20 (FIG. 1) where digital values of signals are placed with at least at 512 Hz discretization frequency. Block (20) is able to collect only signal values or employ software that could be able to produce durations of the heart action periods. Signal transmission from the block (20) to the data formatter (30) is performed after completion of daily data collection adding starting time and completion time (timer). Signals in the format of the selected data from the data formatter (30) though local network sending equipment (40) are transmitted to various computer network receiving equipment (50) which enables their storage in the computer (60) memory (65). Subsequently computer processes data received and transmit them to the report block (70) and printer.

Figure 6:
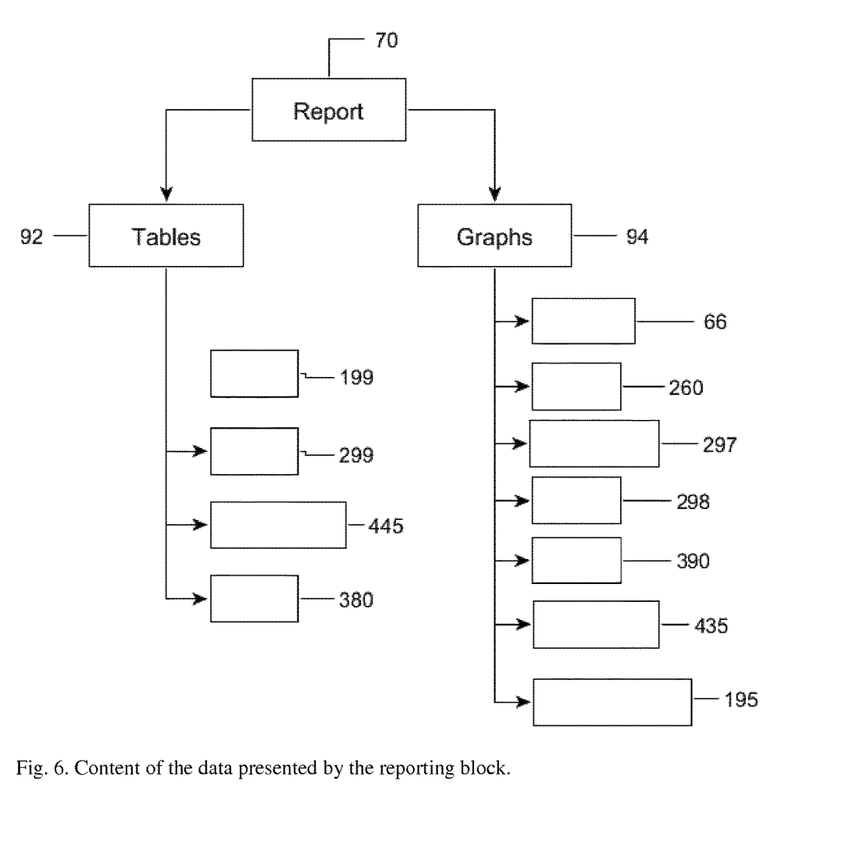
FIG. 6: Content of the data presented by the reporting block.
Figure 7:
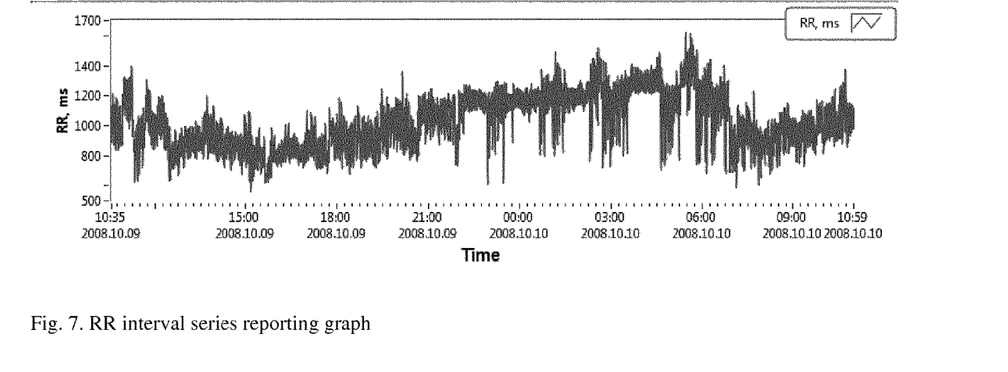
FIG. 7: RR interval series reporting graph.
Figure 8:
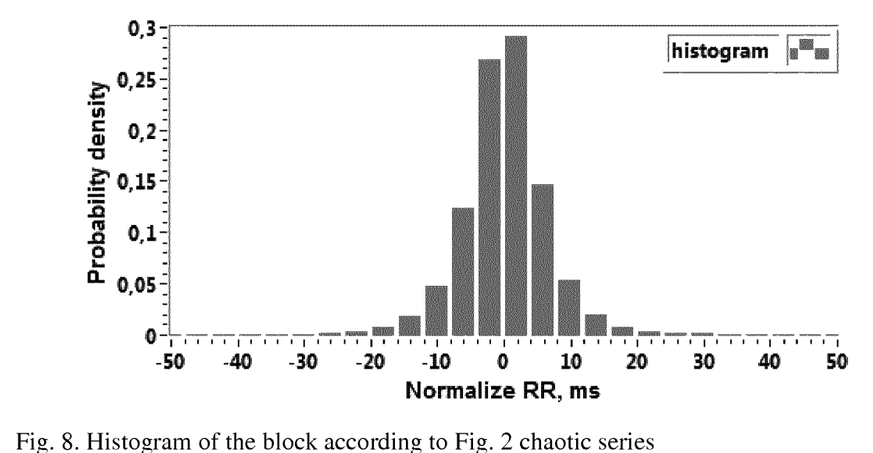
FIG. 8: Histogram of the block according to FIG. 2 chaotic series.
Figure 9:
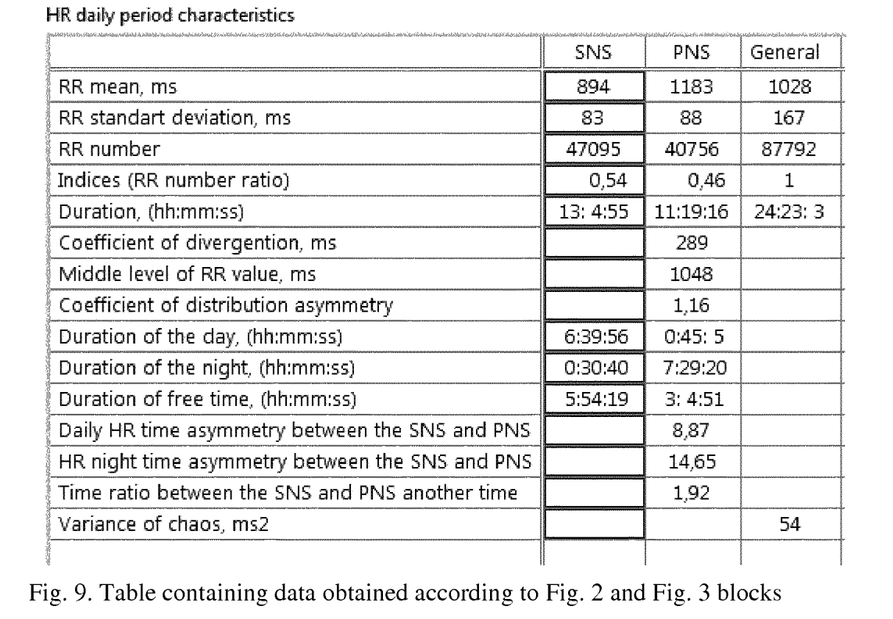
FIG. 9: Table containing data obtained according to FIG. 2 and FIG. 3 blocks.

The order of the processing of data downloaded to the memory 65 is detailed below. The RR interval series file from the memory 65 is transferred directly to the report block 70 in the form of RR interval report graph RR-Graf, 66 (FIG. 6, FIG. 7) and enters block for heart rhythm purification. Chaotic part identification and series interpolation 100 (FIG. 1, FIG. 2) where artifacts and arrhythmias are removed from RR series (100), RR series chaotic parts are identified (120) and chaotic series chaos RR, (130) is identified and separated from RR series (140); interpolation, resample and normalization (160) and analysis of chaotic parts (190) are also performed resulting in chaotic series histogram chaos_HistGraf, 195 (FIG. 8) and completion of time distribution table laik_Lent 1, 199 (FIG. 9).

Figure 2:
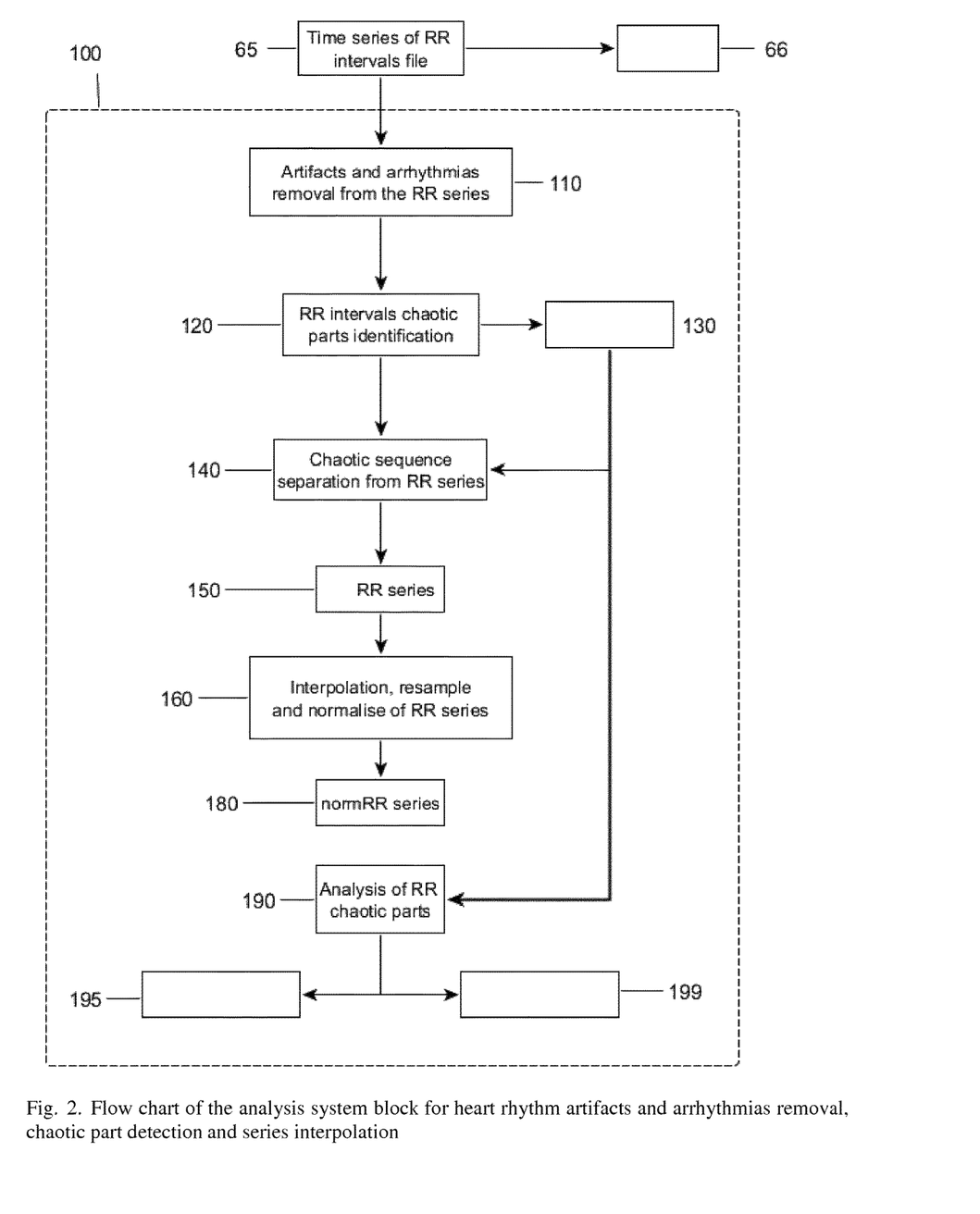
FIG. 2: Flow chart of the analysis system block for heart rhythm artifacts and arrhythmias removal, chaotic part detection and series interpolation.

Artifact and arrhythmias removal (110) from circadian RR interval series (65) is executed using wavelet transform method (Stephane Mallat. A Wavelet Tour of Signal Processing, Third Edition: The Sparse Way. Academic press of Elsevier, 805p., 2009, ISBN-13: 978-0123743701), which separates slow fluctuations from RR interval series and store them in the memory (65). Besides slow fluctuations series, mean (LxRR) of frame and standard deviation (LsRR) are calculated in every RR interval series with moving time frame (L.gtoreq.300 s) while moving through a single memory address. RR interval values overriding LxRR+ 3*LsRR boundaries are adjusted at every step by replacing them with new LxRR values. After completion of movement, slow fluctuation RR interval series obtained after wavelet transform is added to the new adjusted RR interval series, and clean circadian RR interval series is obtained (den RR, 150) which is stored in the memory 65.

Obtained RR interval series (denRR, 150) using obtained real time series (timer) is interpolated by cubic Hermite interpolation method (described Burden, Richard L.; Faires, J. Douglas (2004). Numerical Analysis. Belmont: Brooks/Cole. P. 872. 2011) with the period equal or shorter than 0.5 second. Mean (xRR) and standard deviation (sRR) of the obtained new RR data sequence is calculated and stored in the memory 65 for future calculations. This series is normalized (average is subtracted and result is divided by two) and final RR data series (norm RR) ready for analysis is obtained.

Figure 3:
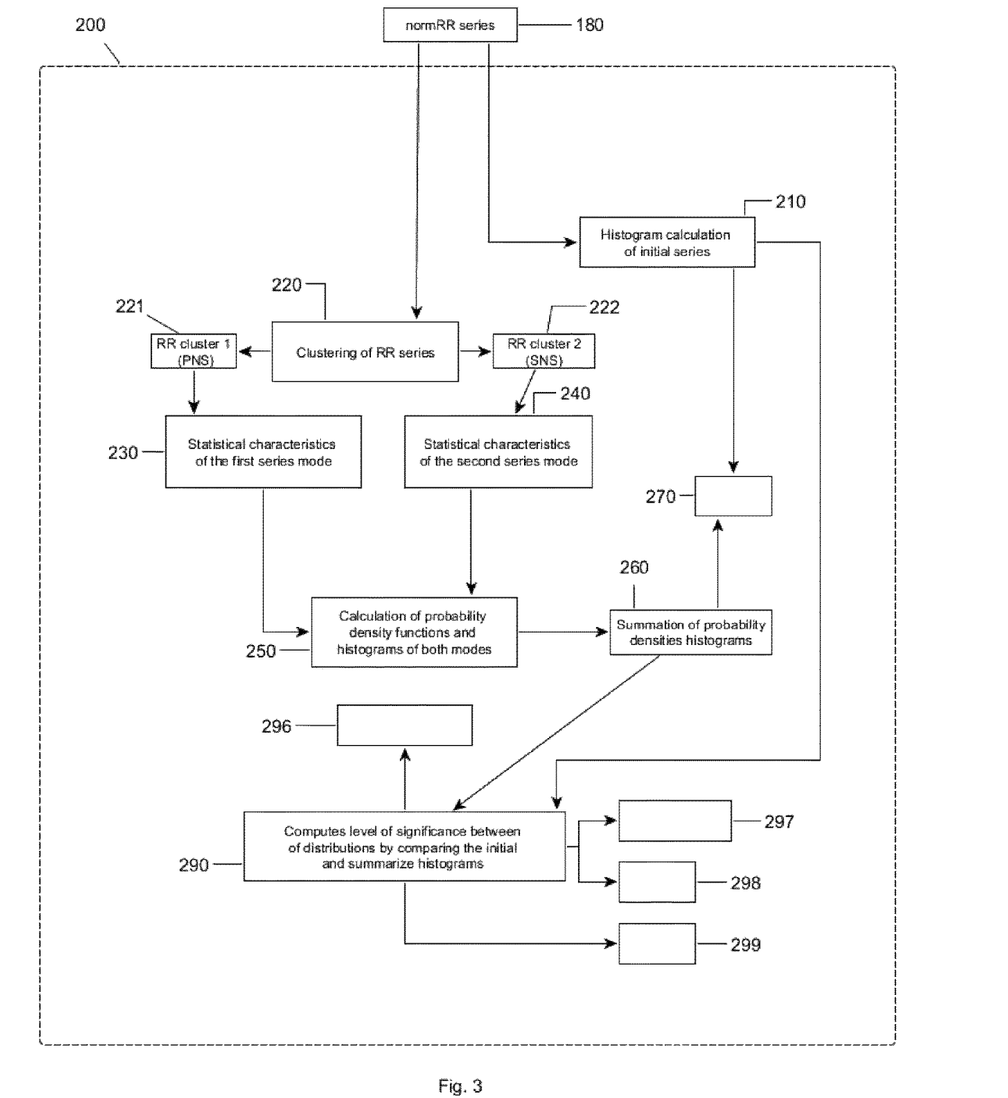
FIG. 3: Flow chart of the block for the heart rhythm bimodal distribution and analysis of the detected modes.
Figure 10:
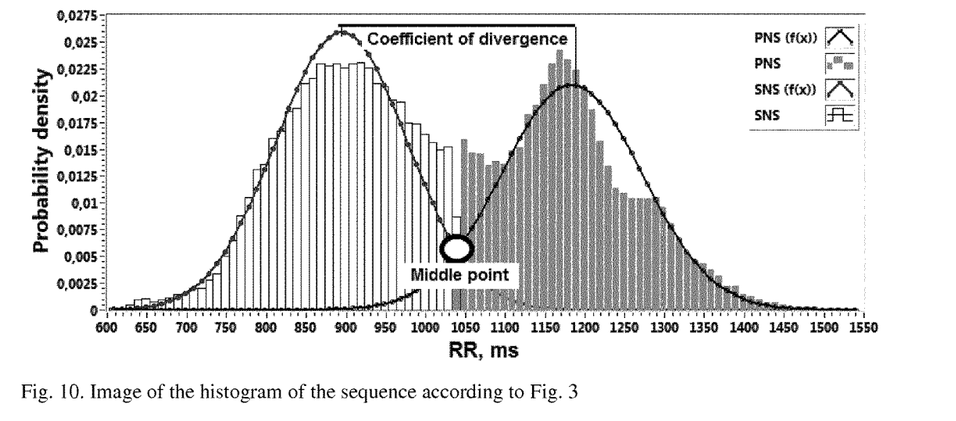
FIG. 10: Image of the histogram of the sequence according to FIG. 3.

Block for the heart rhythm bimodal distribution and analysis of the detected modes 200 (FIG. 3) executes calculation of the initial histogram series (210) from normalized RR data series (norm RR, 180) with 60-80 graduation marks. Their number is determined by selected histogram interval delta with values between 12 and 15 ms. Results are presented in graph form (histGraf, 270) (FIG. 10). Using k-means clustering method (Spaeth, Helmuth. Cluster-Analyse-Algorithmen zur Objektklassifizierung and Datenreduktion, Verfahren der Datenverarbeitung, Muenchen: R. Oldenbourg, P. 71, 1975), RR series clustering is carried out when normRR series (180) is divided into two clusters (modes): first mode is RR cluster 1 (221) with low heart rate frequency, and second mode is RR cluster 2 (222) with high heart rate frequency. For this mode (230) No 1 mean xRR1, standard deviation sdRR1 and number of RRs are calculated. Using the same interval delta out of xRR1 and sdRR1, probability density function PDF1 is calculated which is normalized with respect to the whole norm RR series length (No 0) (240) using normalization coefficient NO 1/No 0 (240). For the second mode these calculations are repeated, however, using their mean xRR2, standard deviation sdRR2 and normalization coefficient NO 2/No 1 (250). Both density functions are analyzed in the form of histogram; they are summarized (260) and presented as the graph together with histogram graph (histGraf, 270) (FIG. 10). Using chi-square criteria distribution, consistency between aggregated and initial (210) histogram is determined and calculation of the aggregate histogram of both modes is performed (290). Maximum values of peaks equal to xRR1 and xRR2 are found at aggregated histogram as well as their equivalence in the graduation marks of the RR value histogram. The difference between xRR1 and xRR2 is equal to the coefficient of divergence between PNS and SNS (FIG. 10), which shows the level of the dominance of both parts of ANS in the heart rhythm tonic regulation. A level point of intersection of probability densities of xRR1 and xRR2 values is determined in the aggregate histogram as well as its equivalent to the graduation mark of the RR histogram (FIG. 10), which divides initial normRR sequence histogram histGraf (270) into two parts where numbers of RR intervals nrRR1 and nrRR2 are counted as well as their summarized durations sekRR1 and sekRR2. Ratio of nrRR1 and nrRR2 is calculated, which is defined as heart rate coefficient of asymmetry, and calculated ratio of sekRR1 and sekRR2 represent total duration asymmetry coefficient. The point of intersection of both distributions (level point) shows value of the RR interval dividing level of dominance of both parts of ANS (SMS and PNS) or value at which impact of both parts of ANS is equally balanced.

Figure 11:
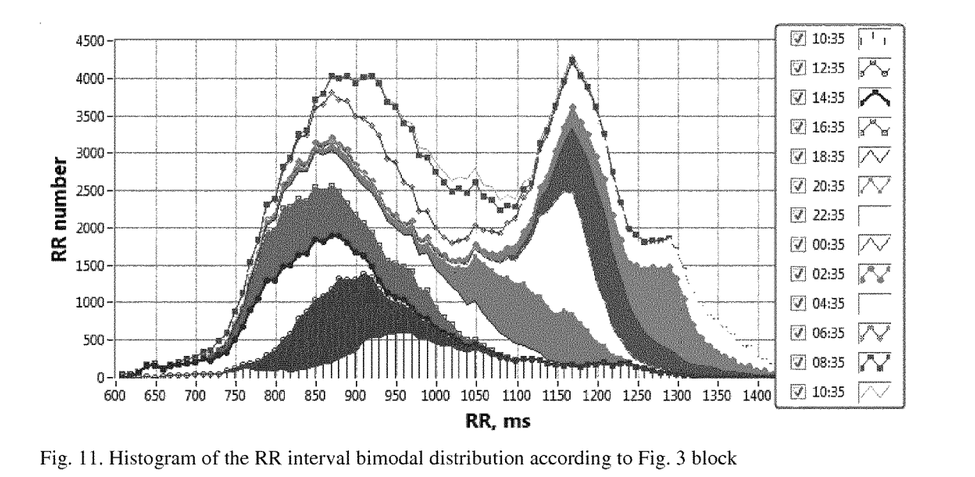
FIG. 11: Histogram of the RR interval bimodal distribution according to FIG. 3 block.
Figure 12:
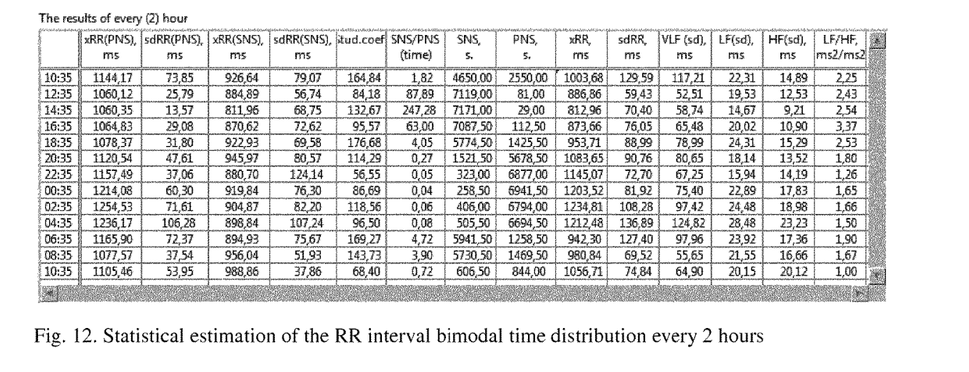
FIG. 12: Statistical estimation of the RR interval bimodal time distribution every 2 hours.

Summary duration times with desirable time frames (e.g., L.gtoreq.1 hour) and RR interval histogram distribution per day presented in the histogram histLaikGraf, 297 (FIG. 11) showing ANS heart rhythm asymmetry 24-hour time course are calculated from the RR intervals of every mode. Statistical calculations of RR intervals are performed at every time frame, and results are presented in the table Laik-Paisk_Lent, 296 (FIG. 12).

Figure 13:
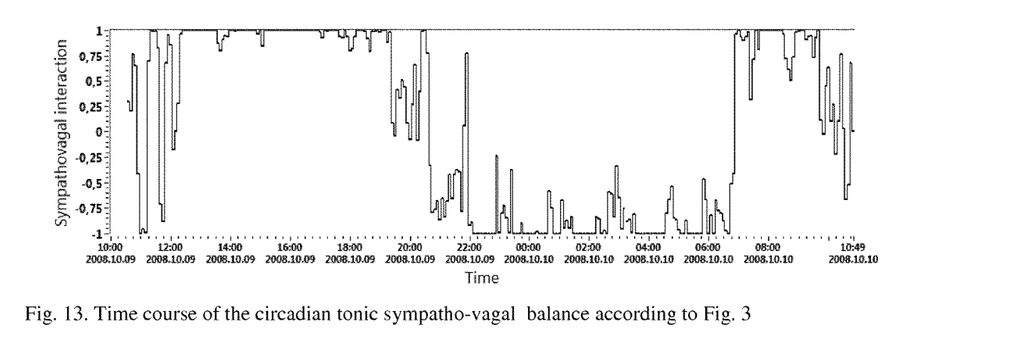
FIG. 13: Time course of the circadian tonic sympatho-vagal balance according to FIG. 3.
Figure 14:
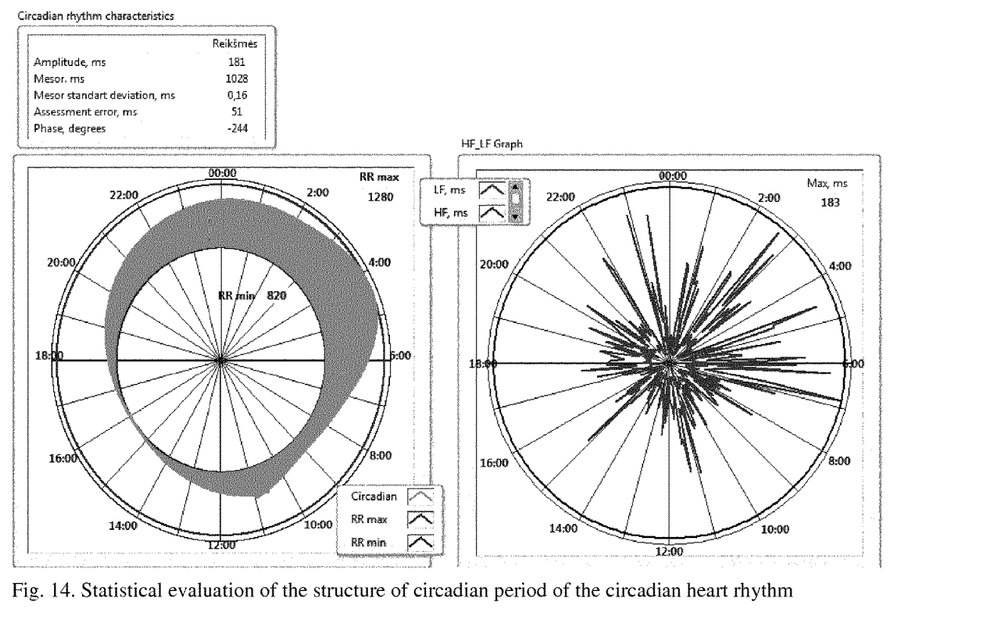
FIG. 14: Statistical evaluation of the structure of circadian period of the circadian heart rhythm.

After figure of one was assigned to any value of RR of the first mode and figure of two was assigned to any value of RR of the second mode they are summarized in the new value frame (l.gtoreq.300 s), the result is multiplied by two, divided by the length of frame and after figure of three is subtracted from the result, normalized sympatho-vagal balance time course laikGraf, 298 (FIG. 13) is obtained. When value equals plus one (+1) is obtained, SNS is totally dominating in the heart rhythm regulation. Values equal to minus one (−1) show that PNS is totally dominating (FIG. 13). Additionally RR interval values in every time frame are also presented in the general table laikLent2, 299 (FIG. 9) as summary calculation.

In the block for the identification of the circadian period of the heart rhythm (FIG. 4), heart rhythm circadian periods are extracted from normalized RR data series (normRR, 180) using continual empirical mode decomposition (Huang transform) (Huang N. E., Shen, Z., Long, S. et al., The Empirical Mode Decomposition and the Hilbert Spectrum for Nonlinear and Non-Stationary Time Series Analysis. Proc. Royal Soc. London Series A, 1998, vol. 454, pp. 903-995; Ming-Chya Wu and Chin-Kun Hu. Application of Empirical Mode Decomposition to Cardiorespiratory Synchronization. S. K. Dana et al. (eds.), Complex Dynamics in Physiological Systems: From Heart to Brain, Understanding Complex Systems, Springer Science+Business Media B. V. 2009). Intrinsic mode functions (IMF) are identified in the RR data series (normRR, 180) and they are gradually removed from every occurred residual interval series. When less than three peaks and less than four valleys remain in the residual series, operation is terminated. Residual series is the heart rhythm circadian period series (cirkRR). By applying empirical mode decomposition (EMD) (Huang transform) method to RR data series (180), its two components are extracted: RR values tonic circadian HR period and residual fluctuations of RR values that are shorter than circadian period.

Figure 4:
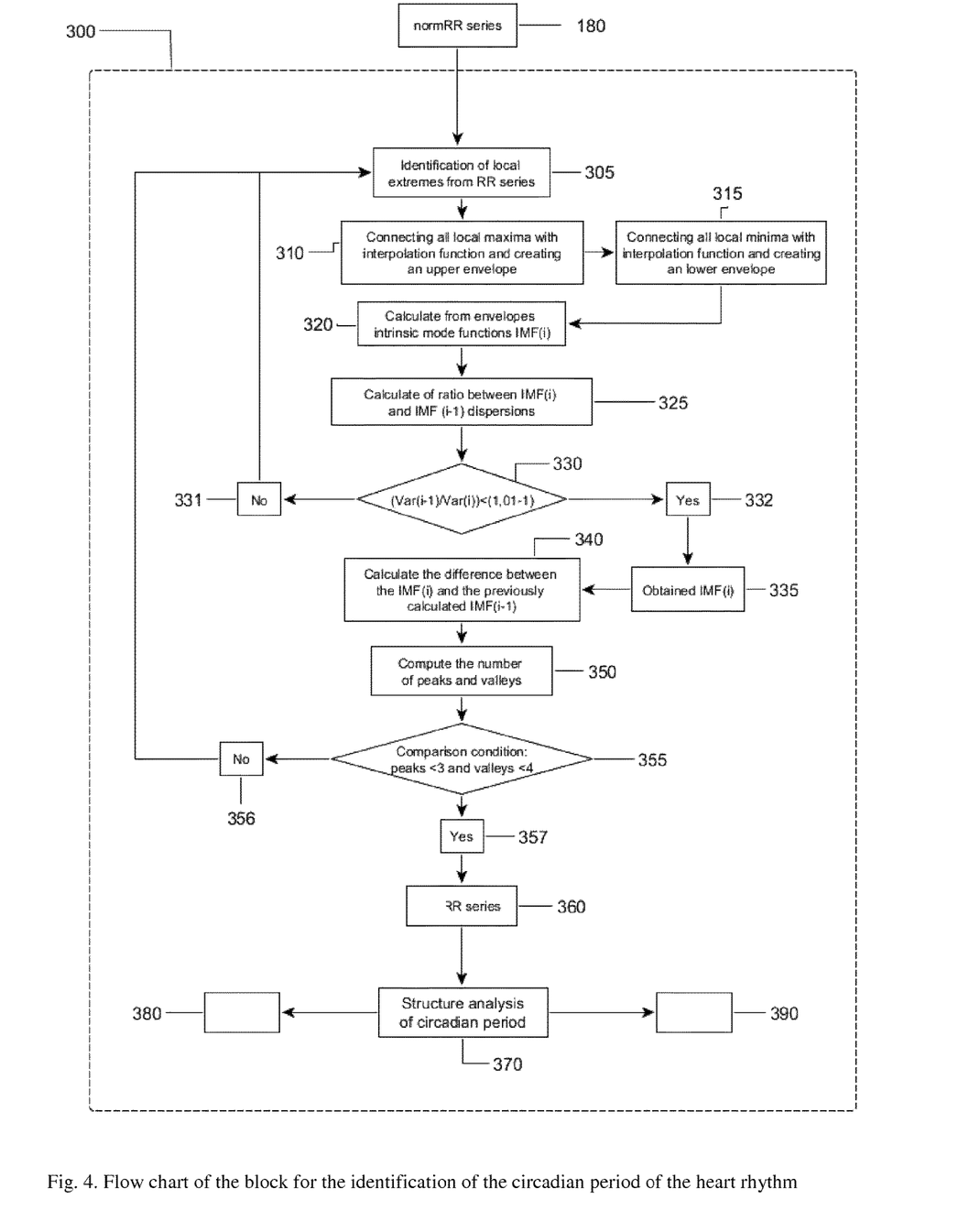
FIG. 4: Flow chart of the block for the identification of the circadian period of the heart rhythm.

The following stages and steps are performed applying empirical mode decomposition:

1. By applying first derivative local extreme points (305) are identified in the whole RR data (normRR, 180) time line x(t).

2. All maxima are separately connected (310) by cubic splines using cubic Hermite polynomial interpolation (Burden, Richard L.; Faires, J. Douglas (2004). Numerical Analysis. Belmont: Brooks/Cole. 872 p. 2011) resulting in the formation of upper envelope curve, u(t).

3. All local minima are connected (315) applying Hermite interpolation procedure for local minima resulting in the formation of lower envelope curve l(t).

4. The data mean for both envelope curves is calculated using operation m(t)=[u(t)+l(t)/2] and interim intrinsic mode function IMF(t), h(t) (320) is determined by calculating the difference between data x(t) and obtained envelope values of mean m(t), h(t)=x(t)−m(t). IMF (1) is subtracted from the series normRR, 180 for the first time.

5. INF(i) series, h(t) dispersion and ratio with previously calculated IMF(i−1) dispersion Var(i−1) are calculated in order to achieve reliable accuracy of calculation with the probability of 0.01 (Fisher's dispersion distribution coefficient).

6. Steps 1-5 are repeated with interim intrinsic mode function IMF(i), h(t) for as long as its magnitude of dispersion compared (330) with previously obtained IMF(i−1) match the criteria (331) (more than 0.01).

7. When restriction (332) indicated in the 6.sup.th step is matched after previous steps, this stage and extraction of the interim IMF(i) is completed; this interim IMF(i) taken as a last IMF(i) component, c(t) found at this stage.

8. Next stage repeats steps 1-7 for remaining series r(t): r(t)=x(t)−c(t) (340), where r(t) is considered as a new time series, x(t).

9. The number of peaks and valleys in the new time series x(t) is determined.

Figure 15:
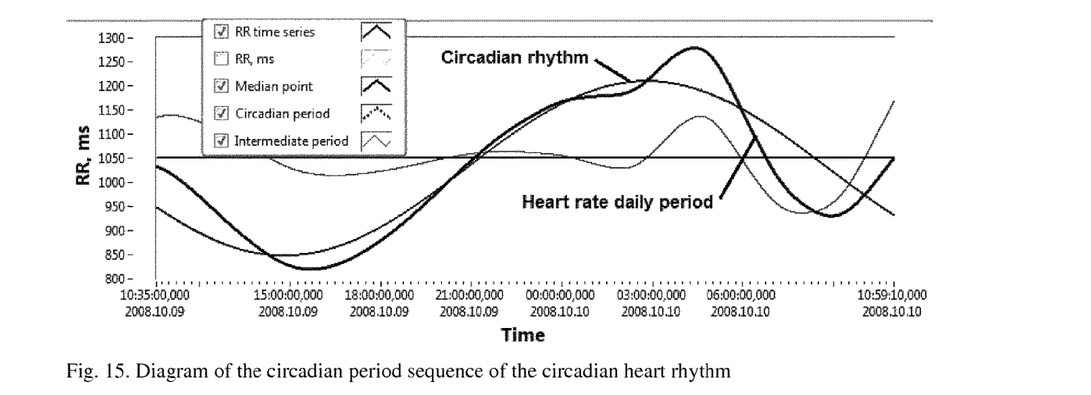
FIG. 15: Diagram of the circadian period sequence of the circadian heart rhythm.

Stages repeat steps 1-9 every time, checking number of peaks and valleys (355) as long as restriction (355) is matches matched, and these steps are completed when residual time series contains less than three peaks and less than four valleys (357), and thus heart rhythm circadian period series (cirkRR, 360) is obtained which may have been close to sinusoid wave shape. To obtain heart rhythm circadian period sinusoid-shaped curve, multicomponent cosinor calculation method is applied (Nelson W, Tong Y L, Lee J K, Halberg F. Methods for cosinor-rhythmometry. Chronobiologia. 1979, 6(4), 305-323; Cornelissen G. Cosinor-based rhythmometry. Theor Biol Med Model. 2014, 11; 11(1):16; Bingham C, Arbogast B, Cornelissen Guillaume G, Lee J K, Halberg F: Inferential statistical methods for estimating and comparing cosinor parameters. Chronobiologia 1982, 9:397-439). Cosinor method allows obtaining heart rhythm circadian period curve and performs its structure analysis (370) extracting additional elements of smaller period. Cosinor method allows calculating structure indicators of the circadian heart rhythm circadian period: mean amplitudes of the circadian period and its components (MESOR), wave amplitudes, acrophases, their duration and dispersion. Statistical evaluation of obtained parameters is performed using Fisher's reliability criterion (F-test), and results are presented in the table cirkLent, 380 (FIG. 6) and also presented in graph form cirkGraf, 390 (FIG. 15).

In the block for the analysis of the SNS and PNS regulation criteria of the heart rhythm variable part (FIG. 5), first RR variable part separation is performed (405), which is obtained by subtraction of heart rhythm circadian period and its components series (cirkRR, 365) (FIG. 3) from normalized RR data series (normRR, 180) (FIG. 2). New interim RR data series (flucRR, 410) obtained represents RR interval frequencies that are higher than circadian fluctuations.

Figure 5:
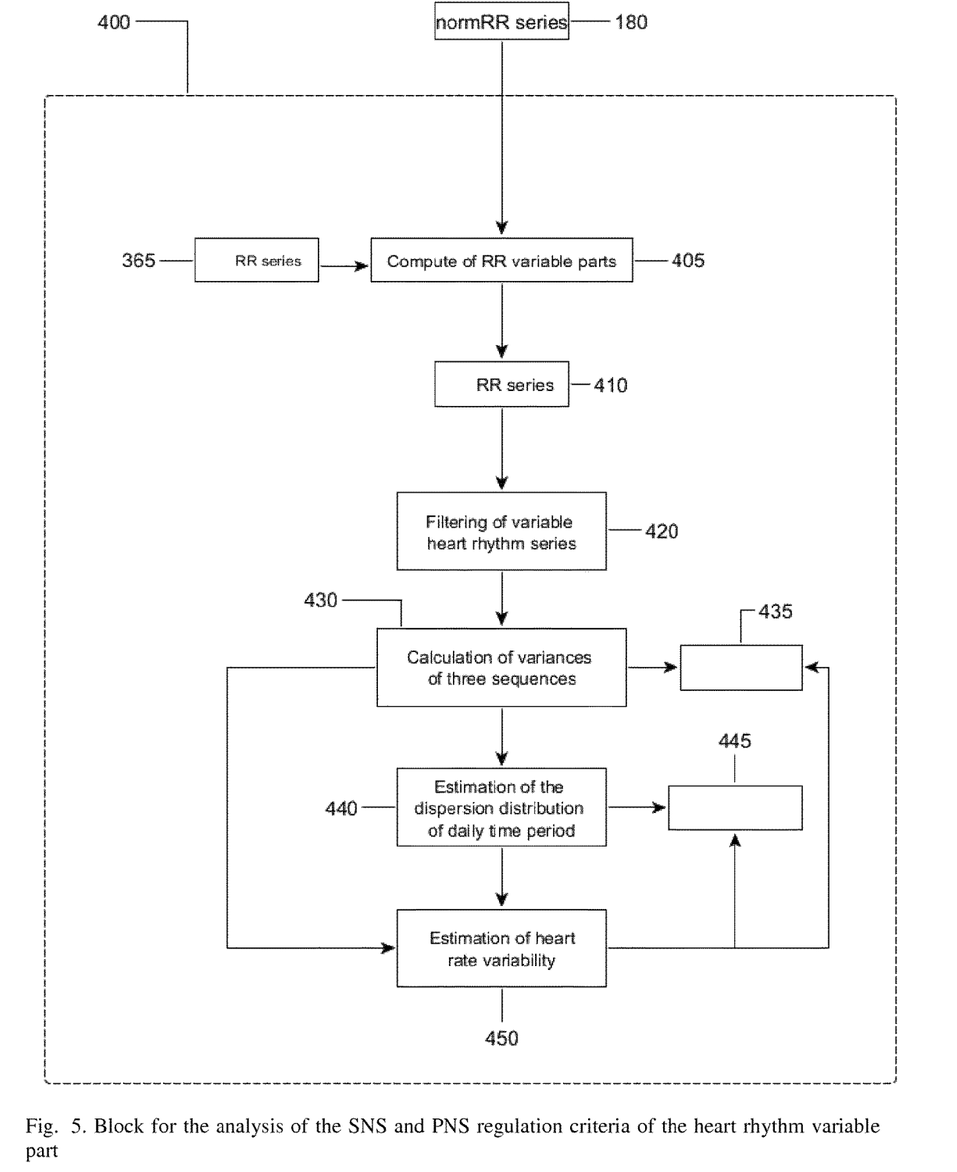
FIG. 5: Block for the analysis of the SNS and PNS regulation criteria of the heart rhythm variable part.

Using classic infinite impulse response three-filter restriction method (Butterworth, Kaiser et al.), first of all filtering of the variable heart rhythm sequence (420) is performed, determining three RR interval time series: very low frequency (VLF), low frequency (LF) and high frequency (HF).

Figure 16:
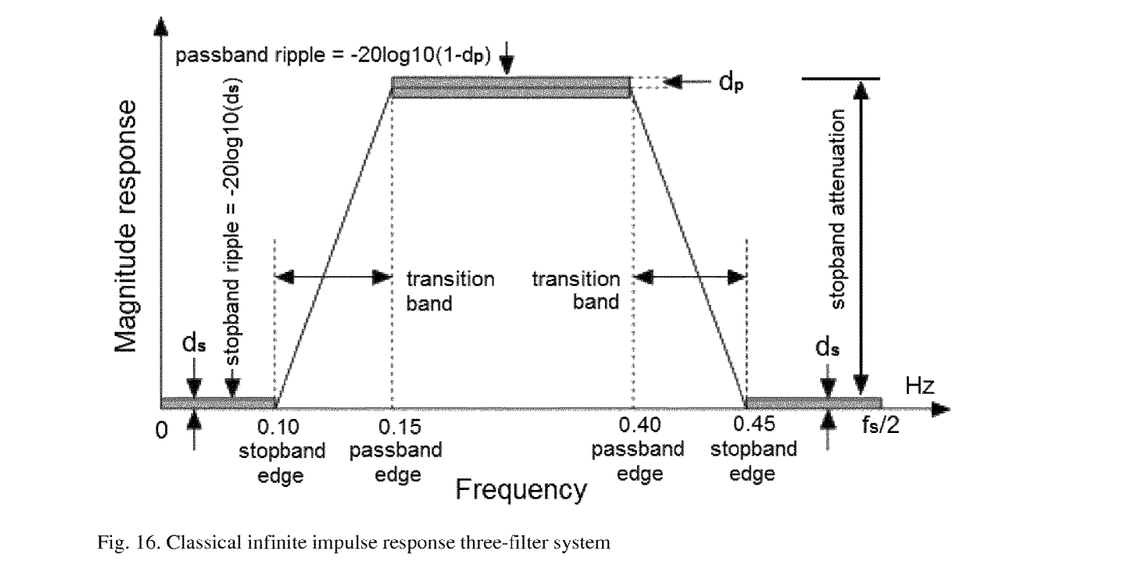
FIG. 16: Classical infinite impulse response three-filter system.

Further, by applying three-filter restriction system (FIG. 16), analysis of the variability of fluctuating RR data series is performed:

1. For the very low frequency filter (VLF, from 0 Hz to 0.04 Hz) determining passband edge frequency equal to 0.035 Hz and stopband edge frequency equal to 0.04 Hz.

2. For low frequency band filter (LF 0.04-0.15 Hz) determining stopband edge frequency at low frequency side equal to 0.035 Hz, and at high frequency side equal to 0.0155 Hz, passband edge frequency at low frequency side equal to 0.04 Hz, and at high frequency side equal to 0.15 Hz.

3. For the high frequency band filter (HF, 0.15-0.40 Hz) determining stopband edge frequency at low frequency side equal to 0.145 Hz, and at high frequency side equal to 0.45 Hz, passband edge frequency at low frequency side equal to 0.15 Hz, and at high frequency side equal to 0.40 Hz.

4. Equal conditions for all filters determining stopband percent ripple equal or larger than 60 dB and passband percent ripple equal and lower than 0.01 dB.

5. Specified filter characteristics allow obtaining constant result regardless of an investigator's choice of available classic infinitive response filters for the filtering of circadian heart rhythm, except filters for short time series because all these filters possess different distortions of the result's initial sections of series.

6. In order to avoid these distortions, every defined time series is filtered twice, first direct filtering is performed, and second filtering is performed by turning around memory addressing of the reversely obtained series and by turning around filtering results once more. This helps to avoid violation of the structure of initial time in the RR interval series.

7. After filtering, every series is multiplied by median standard deviation of the initial RR sequence.

Dispersion and mean standard deviation values that selectively may be expressed by dispersion values (ms.sup.2) or amplitude values (ms) are calculated in the selected time frames (l.gtoreq.100 s) of the three series obtained after filtering. To evaluate these dispersions and mean standard deviations, their distribution in the desirable time frame within circadian time frame is calculated. Obtained results represent SNS and PNS involvement level in the regulation of the phase changes of heart rhythm throughout 24 hours.

To evaluate variability of heart rhythm (450), ratio of dispersions found in low frequency (LF) and high frequency (HF) bands is calculated showing changes in SNS and PNS phase balance within 24 hours in every time frame (No Authors Listed. Heart Rate Variability: Standards of Measurement, Physiological Interpretation, and Clinical Use, Circulation, 93, (1996), pp. 1043-1065; Heart Rate Variability: Standards of Measurement, Physiological Interpretation, and Clinical Use, European Heart Journal, 17, Prepared by the Task Force of The European Society of Cardiology and The North American Society of Pacing and Electrophysiology; published by the American Heart Association, Inc.; European Society of Cardiology, (1996), pp. 354-381).

Time course of the heat rhythm variability is further presented in the table (laikSpekGraf, 435) (FIG. 17) and table (laikSpek_Lent, 445) (FIG. 12).

The invention claimed is:

1. An analysis system for analyzing a balance of a circadian heart rhythm autonomic nervous system wherein the analysis system increases accuracy of the analysis of HRV results and adds new HR regulation criteria to the analysis outcomes, wherein the system comprises:
    a RR interval collection block;
    tools for artifact and arrhythmias removal from RR interval series;
    an identifier for circadian period and RR interval series; and
    a data analyzer finding sympathetic and parasympathetic nervous system balance, wherein the tools are configured to perform the following after artifact and arrhythmias removal from RR interval series:
        1) identify a chaotic part of the RR interval series and analysis of the chaotic part;
        2) separate the chaotic part from the RR interval series and aquire a clean circadian RR series;
        3) aquire a normalized RR interval series using interpolation, resampling and normalization;
        4) analyze the heart rate bimodal distribution and modes of the normalized RR interval series;
        5) identify a heart rate circadian period in the normalized RR data series;
        6) analyze the heart rhythm variable part SNS and PNS regulation indicators in the normalized RR data series; and
        7) generate a report on obtained results in graph and tabular form.

2. The analysis system according to claim 1, wherein the tools for artifact and arrhythmias removal from RR series performs chaotic series separation from RR series and obtains clean circadian RR interval series using a wavelet transform method.

3. The analysis system according to claim 1, wherein to obtain a normalized data series, interpolation of circadian RR interval series is performed using cubic Hermite interpolation.

4. The analysis system according to claim 1, wherein the following are performed by the heart rhythm bimodal distribution and analysis of the modes detected in the normalized RR data series block:
    calculate an input histogram sequence out of normalized RR data series and histogram graphic presentation;
    cluster a normalized RR data series into two RR clusters (modes) of which the RR cluster 1 (first mode) involves low heart rhythm frequencies and RR cluster 2 (second mode) involves high heart rhythm frequencies;
    calculate statistical characteristics of the first mode series and second mode series;
    calculate probability density functions for both modes and their histograms;
    summate probability density histograms and their graphic presentation;
    determine reliability of the compliance of the distributions between summary histogram and input histogram using chi-square criterion and calculation of the summary histogram for both modes;
    determine a divergence coefficient in the summary histogram of both modes;
    determine a skewness coefficient of the heart rate and skewness coefficient of the total time in the input histogram;
    present statistical calculations in tabular form;
    present circadian time distribution of the RR interval within both modes in graphic form;
    present the normalized time course of the circadian tonic sympatho-vagal balance in graphic form;
    present the values of results of summary calculations of the values of RR interval analysis in tabular form.

5. The analysis system according to claim 4, wherein the heart rhythm bimodal distribution and analysis of the modes detected in normalized RR data series by a block is clustering normalized RR data series into two groups using a k-means clustering method.

6. The analysis system according to claim 1, wherein the block for heart rhythm circadian period identification within RR data series:
- isolates the heart rhythm circadian period performing continual empirical mode decomposition involving detection of interim modes and their gradual elimination from every residual RR interval series;
- obtains the heart rhythm circadian period series and analyzes the circadian period structure.

7. The analysis system according to claim 6, wherein the block for heart rhythm circadian period identification within RR data series analyzes the circadian period structure using a cosinor calculation method and includes statistical evaluation of parameters obtained, presenting them in tabular and graph forms.

8. The analysis system according to claim 1, wherein the block for the analysis of the heart rhythm variable part SNS and PNS regulation criteria performs the following:
- separates the RR variable part which is achieved by subtraction of the heart rhythm circadian period from normalized RR data sequence;
- filters the variable heart rhythm series when three RR interval time series of different frequencies are separated;
- calculates the dispersion and mean standard deviations and of three RR intervals time series;
- evaluates heart rhythm variability;
- presents the evaluation of the heart rhythm variability in graphic and tabular forms.

9. The analysis system according to claim 8, wherein the variable heart rhythm series filter employs an infinite impulse response three-filter restriction method determining very low frequency (VLF), low frequency (LF) and high frequency (HF) RR interval time series.

10. The analysis system according to claim 9, wherein the block for the analysis of the heart rhythm variable part SNS and PNS regulation criteria performs the following evaluation of heart rhythm variability:
- for the very low frequency filter determining passband edge frequency equal to 0.035 Hz and stopband edge frequency equal to 0.04 Hz;
- for low frequency band filter determining stopband edge frequency at low frequency side equal to 0.035 Hz, and at high frequency side equal to 0.0155 Hz, passband edge frequency at low frequency side equal to 0.04 Hz, and at high frequency side equal to 0.15 Hz;
- for the high frequency band filter determining stopband edge frequency at low frequency side equal to 0.145 Hz, and at high frequency side equal to 0.45 Hz, passband edge frequency at low frequency side equal to 0.15 Hz, and at high frequency side equal to 0.40 Hz.

11. The analysis system according to claim 10, wherein, in the block for the analysis of the heart rhythm variable part SNS and PNS regulation criteria, evaluation of the heart rhythm variability is performed by calculation of the dispersion ratio for every time frame within low frequency and high frequency bands presenting phase balance of SNS and PNS changes.

12. The analysis system according to claim 10, wherein the block for the analysis of the heart rhythm variable part SNS and PNS regulation criteria performs the following evaluation of heart rhythm variability:
- for the very low frequency filter from 0 Hz to 0.04 Hz, determining passband edge frequency equal to 0.035 Hz and stopband edge frequency equal to 0.04 Hz;
- for low frequency band filter 0.04-0.15 Hz determining stopband edge frequency at low frequency side equal to 0.035 Hz, and at high frequency side equal to 0.0155 Hz, passband edge frequency at low frequency side equal to 0.04 Hz, and at high frequency side equal to 0.15 Hz;
- for the high frequency band filter 0.15-0.40 Hz determining stopband edge frequency at low frequency side equal to 0.145 Hz, and at high frequency side equal to 0.45 Hz, passband edge frequency at low frequency side equal to 0.15 Hz, and at high frequency side equal to 0.40 Hz.

* * * * *